United States Patent [19]

Blattner

[11] Patent Number: 4,551,283

[45] Date of Patent: Nov. 5, 1985

[54] PROCESS FOR ISOLATING 2-NAPHTHYLAMINE-3,6,8-TRISULFONIC ACID IN THE FORM OF THE MONOPOTASSIUM OR MONOAMMONIUM SALT

[75] Inventor: Rudolf Blattner, Rheinfelden, Fed. Rep. of Germany

[73] Assignee: Ciba Geigy AG, Basel, Switzerland

[21] Appl. No.: 638,845

[22] Filed: Aug. 8, 1984

[30] Foreign Application Priority Data

Aug. 17, 1983 [CH] Switzerland ............... 4486/83

[51] Int. Cl.[4] .......................................... C07C 143/56
[52] U.S. Cl. .................................................. 260/508
[58] Field of Search ....................................... 260/508

[56] References Cited

U.S. PATENT DOCUMENTS 4,348,336 9/1982 Blank et al. ............. 260/508
4,407,762 10/1983 Blank et al. ............. 260/508

Primary Examiner—Nicky Chan
Attorney, Agent, or Firm—Joseph G. Kolodny

[57] ABSTRACT

There is disclosed a process for isolating 2-naphthylamine-3,6,8-trisulfonic acid in the form of the alkali or ammonium salt from the sulfonation mixture resulting from the sulfonation of the corresponding naphthylaminemonosulfonic or -disulfonic acid in oleum, which process comprises starting from a sulfonation mixture which contains the naphthylaminetrisulfonic acid in the form of the monopotassium or monoammonium salt, charging said mixture into water or dilute sulfuric acid such that the concentration of the sulfuric acid in the dilute solution or suspension of the sulfonation mixture is 30 to 77% by weight, simultaneously allowing the temperature to rise to 90° to 125° C., subsequently slowly cooling said solution or suspension to a temperature below 40° C., during said cooling adding at least 0.1% by weight, based on naphthylaminetrisulfonic acid, of a dispersant, and isolating the precipitated monopotassium or monoammonium salt of 2-naphthylamine-3,6,8-trisulfonic acid.

The naphthylaminetrisulfonic acid isolated in this manner in the form of the monopotassium or monoammonium salt from the sulfonation mixture can be used direct for the manufacture of textile dyes.

8 Claims, No Drawings

PROCESS FOR ISOLATING 2-NAPHTHYLAMINE-3,6,8-TRISULFONIC ACID IN THE FORM OF THE MONOPOTASSIUM OR MONOAMMONIUM SALT

The present invention relates to a process for isolating 2-naphthylamine-3,6,8-trisulfonic acid in the form of the monopotassium or monoammonium salt from the sulfonation mixture resulting from the sulfonation of the corresponding naphthylamine-monosulfonic or -disulfonic acid in oleum, and to the monopotassium or monoammonium salt of 2-naphthylamine-3,6,8-trisulfonic acid isolated by said process.

Naphthylaminetrisulfonic acids are important intermediates for the manufacture of dyes. They are ordinarily prepared by sulfonating the corresponding disulfonic acids with oleum.

Further, the trisulfonic acids can also be obtained by disulfonating the corresponding naphthylamine-monosulfonic acids. Thus 2-naphthylamine-3,6,8-trisulfonic acid can be obtained from 2-naphthylamine-6-sulfonic acid and 1-naphthylamine-2,5,7-trisulfonic acid from 1-naphthylamine-5-sulfonic acid [Houben-Weyl, Methoden der organischen Chemie 9, 478–485 (1955)].

The working up procedure up to now has been that the sulfonation mixture is charged into water and the naphthylaminetrisulfonic acid salted out by addition of ammonium sulfate, sodium sulfate or potassium sulfate. In this procedure, in which large amounts of sulfate are required, the naphthylaminetrisulfonic acid is obtained in particular in the form of the diammonium or dialkali salt. Salting out affords products which have a high salt content and are difficult to filter, complicates the recovery of the sulfuric acid and, in addition, causes substantial pollution of the wastewater. It has now been found that the shortcomings of the former procedure for isolating 2-naphthylamine-3,6,8-trisulfonic acid can be avoided if said compound is in the form of the monopotassium or monoammonium salt at the start of working up, further by adjusting the sulfuric acid to a specific concentration when diluting the sulfonation mixture, dispensing with salting out, and slowly cooling the hot dilute solution or suspension so obtained while adding a dispersant. In this working up procedure, the 2-naphthylamine-3,6,8-trisulfonic acid (in the form of the monopotassium or monoammonium salt) is precipitated almost completely in the form of a readily filterable crystal slurry. The waste acid is salt-free and can be worked up without problems.

Accordingly, the present invention provides a process for isolating 2-naphthylamine-3,6,8-trisulfonic acid in the form of the alkali or ammonium salt from the sulfonation mixture resulting from the sulfonation of the corresponding naphthylaminemonosulfonic or -disulfonic acid in oleum, which process comprises starting from a sulfonation mixture which contains the naphthylaminetrisulfonic acid in the form of the monopotassium or monoammonium salt, charging said mixture into water or dilute sulfuric acid such that the concentration of the sulfuric acid in the dilute solution or suspension of the sulfonation mixture is 30 to 77% by weight, simultaneously allowing the temperature to rise to 90° to 125° C., subsequently slowly cooling said solution or suspension to a temperature below 40° C., during said cooling adding at least 0.1% by weight, based on naphthylaminetrisulfonic acid, of a dispersant, and isolating the precipitated monopotassium or monoammonium salt of 2-naphthylamine-3,6,8-trisulfonic acid.

Surprisingly, the working up of the monopotassium or monoammonium salt of 2-naphthylamine-3,6,8-trisulfonic acid from 30 to 77% by weight sulfuric acid in the temperature range below 40° C. permits the isolation of a homogeneous product in simple manner and in high purity and good yield, as said monpotassium or monoammonium salt has a minimum solubility under the stated conditions.

The solubility of the monopotassium salt of 2-naphthylamine-3,6,8-trisulfonic acid in sulfuric acid of different concentration, determined at a temperature of 30° C., can be seen from the following table.

| concentration of $H_2SO_4$ in % by weight | 21.2 | 35.9 | 41.2 | 46.0 | 51.1 | 60.3 | 73.2 | 77.5 | 80.2 | 87.5 |
|---|---|---|---|---|---|---|---|---|---|---|
| amounts of dissolved K-salt in % by weight | 3.5 | 1.6 | 0.4 | 0.2 | ~0.1 | ~0.1 | ~0.1 | 0.6 | 4.4 | >11 |

The monopotassium or monoammonium salt of 2-naphthylamine-3,6,8-trisulfonic acid is obtained either by starting from the monopotassium or monoammonium salt of the corresponding naphthylaminemonosulfonic or -disulfonic acid or by adding to the reaction mixture obtained at the conclusion of the sulfonation an amount of potassium or ammonium sulfate sufficient to form the monopotassium or monoammonium salt. Further, it is also possible to charge the reaction vessel with the required amount of potassium or ammonium sulfate together with the water or dilute sulfuric acid necessary for diluting the sulfonation mixture. Instead of using potassium or ammonium sulfate, it is also possible to use another potassium or ammonium salt or a compound which donates potassium or ammonium ions, for example aqueous ammonia solution.

It is preferred to start from a sulfonation mixture which is obtained by reacting the monopotassium salt of 2-naphthylamine-6,8-disulfonic acid in oleum.

The concentration of the sulfuric acid can be adjusted in any desired manner, for example by stirring the reaction mixture into water which may or may not contain sulfuric acid, or conversely. To dilute the sulfonation mixture, water or dilute sulfuric acid is added in an amount such that, finally, the concentration of sulfuric acid in the aqueous solution or suspension so obtained is from 30 to 77% by weight, preferably from 40 to 70% by weight. These concentrations are based on the liquid phase without solids content. The procedure conveniently is that the reaction vessel is charged with the requisite amount of water or sulfuric acid and the sulfonation mixture is added at a rate such that the dilution heat evolved causes the temperature of the resultant solution or suspension to rise to 90°–125° C. without additional heating or cooling. It will be readily understood that the rate of addition of the sulfonation mixture can also be slower or faster, in which case it is only necessary to adjust the temperature within the indicated range by heating or cooling the solution or suspension.

To obtain a good crystalline form, it is advantageous if the temperature of the dilute sulfonation mixture is in the range from 90° to 125° C. After a residence time of about 1 hour, the mixture is cooled to a temperature below 40° C. with slow stirring. Cooling is preferably effected such that the temperature falls at a rate of 0.2 to 1° C./min. The rate of cooling can be constant, or cooling can be effected in two or more phases in which the rate of cooling is constant but differs from phase to phase. It is advantageous to choose at the start a slower rate of cooling so that a supersaturated solution is not obtained and that the dissolved product crystallises to form as small an amount of fine crystals as possible. Cooling is effected for example via the outer jacket of the agitator vessel or by means of an immersion cooler at a conveniently low stirring rate.

During cooling, a dispersant is added to the solution or suspension of the monopotassium or ammonium salt of 2-naphthylamine-3,6,8-trisulfonic acid. At least 0.1% by weight, preferably 0.2 to 5% by weight, based on naphthylaminetrisulfonic acid, of an anionic or cationic dispersant, but preferably of a nonionic dispersant, is used. Suitable dispersants are also amphoteric surfactants. Depending on the stability of the dispersant to acid, the dispersant is added to the still hot solution or dispersion or at lower temperature. The addition of the dispersant is conveniently made at a temperature below 60° C.

Suitable nonionic dispersants are, in particular, ethylene oxide adducts, preferably alkylphenol, fatty alcohol, fatty amine or fatty acid ethoxylates, or also ethylene oxide/propylene oxide copolymers. Some of the ethylene oxide units in the ethylene oxide adducts can be replaced by propylene oxide units.

Representative examples of ethylene oxide adducts are:
(a) polyadducts of saturated and/or unsaturated $C_6$–$C_{20}$ fatty alcohols with 5 to 30 moles of ethylene oxide per mole of hyxdroxyl group;
(b) polyadducts of $C_4$–$C_{12}$ alkylphenols with 5 to 20 moles, preferably 8 to 15 moles, of ethylene oxide per mole of phenolic hydroxyl group;
(c) polyadducts of saturated and/or unsaturated $C_{14}$–$C_{20}$ fatty amines with 5 to 20 moles of ethylene oxide per mole of amino group;
(d) polyadducts of saturated and/or unsaturated $C_{14}$–$C_{20}$ fatty acids with 5 to 20 moles of ethylene oxide per mole of carboxyl group.

Among these ethylene oxide adducts, the polyadducts specified in (b) are preferred. Good results are also achieved with the polyadducts (a), with those types also being particularly useful which are obtained by addition of ethylene oxide and propylene oxide to fatty alcohols or mixtures of fatty alcohols of different chain length.

Mixtures of the ethylene oxide adducts of (a), (b), (c) and (d) with one another can also be used. These mixtures are obtained by mixing individual reaction products or direct by ethoxylating a mixture of compounds from which the adducts are derived.

Suitable saturated and/or unsaturated fatty alcohols (a) are dodecanol, palmityl alcohol, stearyl alcohol, oleyl alcohol or tallow fatty alcohol, preferably hexanol, 2-ethylhexanol and decanol.

The alkylphenols in (b) are butylphenol, hexylphenol, and preferably isooctylphenol, p-tert-octylphenol, nonylphenol and dodecylphenol.

In addition to stearylamine, examples of suitable fatty amines in (c) are palmitylamine and, in particular, oleylamine.

Examples of saturated and/or unsaturated fatty acids in (d) are palmitic acid, in particular stearic acid and oleic acid.

The ethylene oxide adducts are known or they can be prepared by methods which are known per se (q.v. N. Schönfeldt, Grenzflächenaktive Aethylenoxid-Addukte; Wissenschaftliche Verlagsgesellschaft mbH, Stuttgart, 1976).

Ethylene oxide/propylene oxide copolymers are e.g. copolymers having a central propylene glycol unit and a molecular weight of 1000 to 10,000.

The anionic dispersants are the commercially available dispersants employed for aqueous suspensions and dispersions, e.g. condensates of aromatic sulfonic acids with formaldehyde, e.g. condensates of naphthalenesulfonic acid and formaldehyde, or lignosulfonates, e.g. the compounds obtainable under the common name sulfite lye.

Cationic surfactants are e.g. quaternary alkylammonium halides containing at least one $C_8$–$C_{25}$alkyl radical, and long-chain alkylpyridinium halides.

Amphoteric surfactants employed in the process of this invention are in particular those of the betaine type, for example betaine itself as anhydride, hydrochloride or also monohydrate.

Owing to the addition of dispersant, the dilute sulfonation mixture is still readily stirrable even at temperatures below 30° C. and the 2-naphthylamine-3,6,8-trisulfonic acid monopotassium or monoammonium salt is obtained in a form which can be easily filtered.

Once the dilute sulfonation mixture is cooled to a temperature below 40° C., in general to a temperature in the range from 10° to 30° C., as cooling to temperatures below 10° C. is uneconomic, the almost completely precipitated monopotassium or monoammonium salt of 2-naphthylamine-3,6,8-trisulfonic acid is isolated from the mother liquor. This is conveniently done by filtration. The filter cake so obtained, which contains sulfuric acid, can be purified by washing with 30 to 70% sulfuric acid and dried. The potassium or ammonium salt of 2-naphthylamine-3,6,8-trisulfonic acid is obtained in high purity, so that it is also possible to process it further direct, for example to dyes, without any additional purification operations for removing unwanted by-products.

The process of the present invention can be carried out for example as follows:

An agitator vessel is charged with the requisite amount of water for diluting the sulfonation mixture to a sulfuric acid concentration to 40 to 70% by weight. Then the sulfonation mixture obtained in known manner by sulfonating the monopotassium salt of 2-naphthylamine-6,8-disulfonic acid is added, and the temperature rises to about 100°–115° C. The hot suspension, which contains some of the product in dissolved form, is subsequently cooled at a rate of about 0.5° C./min and a nonionic dispersant (about 1% by weight, based on naphthylaminetrisulfonic acid) is added at a temperature of about 50° C. Once the temperature has reached about 25° C., the monopotassium salt of naphthylaminetrisulfonic acid is isolated by filtration in crystalline form. It is not necessary to give the filter cake a washing-off. The isolated product is distinguished by high purity and the concentration of by-products is less than 0.5% by weight.

The quality of the 2-naphthylamine-3,6,8-trisulfonic acid obtained in the form of the monopotassium or monoammonium salt by the process of this invention is conspicuously better than that of the free trisulfonic acid, or also of the dipotassium or diammonium salt or the mixture of potassium and ammonium salts, when isolated by salting out. In addition, an increase in yield of about 5% is obtained.

The invention is illustrated by the following Example, in which percentages are by weight.

EXAMPLE (a) Sulfonation: While blanketing with nitrogen, 1688.5 g of the monopotassium salt of 2-naphthylamine-6,8-disulfonic acid are charged into 6020 g of about 40% oleum (prepared from 3580 g of 25% and 2440 g of 66% oleum) such that the temperature rises only slowly. After addition of the total amount of the disulfonic acid monopotassium salt, the reaction mixture is heated to a temperature of about 140° C. After a reaction time of 5 to 6 hours the sulfonation mixture is cooled and working up is commenced.

(b) Isolation: For working up, the sulfonation mixture is slowly run into 9000 g of water which has first been warmed to 30° C. The temperature rises to 105° C. and is thereafter kept, by cooling, in the range from 105°–109° C. The 98% sulfuric acid (200 g) used for rinsing the reaction vessel in which the sulfonation was carried out is also charged into the above amount of water. The concentration of the sulfuric acid present in the sulfonation mixture is 43–44%. The yellowish brown suspension so obtained is subsequently cooled at a rate of 0.5° C./min to a temperature of 28° C. 15 g of p-tert-octylphenol ethoxylate (p-tert-octylphenol +8.2 mmoles of ethylene oxide) are added to the reaction mixture at about 50° C. When the filtration temperature has been reached, the precipitated monopotassium salt of 2-naphthylamine-3,6,8-trisulfonic acid is isolated by filtration and the filter cake is suction dried.

Yield: 2740.5 g of 70% product which contains sulfuric acid (92% of theory). Concentration of by-products: <0.5%.

By carrying out the same procedure, but using one of the following dispersants in a concentration of 0.2%, based on the reaction mixture, instead of p-tert-octylphenol ethoxylate, there is also obtained a non-thixotropic, or only slightly thixotropic, crystal slurry which is easy to filter. The dispersant is, on the one hand, a further nonionic surfactant, viz. a $C_6$–$C_{10}$ fatty alcohol ethoxylate/propoxylate and, on the other, a cationic surfactant, viz. N,N-dimethyl-N-benzyl-$C_8$–$C_{18}$alkylammonium chloride.

What is claimed is:

1. A process for isolating 2-naphthylamine-3,6,8-trisulfonic acid in the form of the monopotassium or monoammonium salt from the sulfonation mixture resulting from the sulfonation of the corresponding naphthylaminemonosulfonic or -disulfonic acid in oleum, which process comprises starting from a sulfonation mixture which contains the naphthylaminetrisulfonic acid in the form of the monopotassium or monoammonium salt, charging said mixture into water or dilute sulfuric acid such that the concentration of the sulfuric acid in the dilute solution or suspension of the sulfonation mixture is 30 to 77% by weight, simultaneously allowing the temperature to rise to 90° to 125° C., subsequently slowly cooling said solution or suspension to a temperature below 40° C., during said cooling adding at least 0.1% by weight, based on naphthylaminetrisulfonic acid, of a dispersant, and isolating the precipitated monopotassium or monoammonium salt of 2-naphthylamine-3,6,8-trisulfonic acid.

2. A process according to claim 1, wherein the concentration of sulfuric acid in the dilute aqueous solution or suspension of the sulfonation mixture is 40 to 70% by weight.

3. A process according to claim 1, wherein the hot dilute solution or suspension of the sulfonation mixture is cooled at a rate of 0.2° to 1° C./min.

4. A process according to claim 1, wherein the dispersant is added when the temperature of the solution or suspension is below 60° C.

5. A process according to claim 1, wherein the dispersant is added in an amount of 0.2 to 5% by weight, based on naphthylaminetrisulfonic acid.

6. A process according to claim 1, wherein a nonionic dispersant is used.

7. A process according to claim 6, wherein the dispersant is an ethylene oxide adduct or an adduct of ethylene oxide/propylene oxide with an alkylphenol or fatty alcohol or mixture of fatty alcohols.

8. A process according to claim 1, wherein the sulfonation mixture is obtained by reacting the monopotassium salt of 2-naphthylamine-6,8-disulfonic acid in oleum.

* * * * *